US009220568B2

(12) United States Patent
Bromander et al.

(10) Patent No.: US 9,220,568 B2
(45) Date of Patent: Dec. 29, 2015

(54) CATHETER SYSTEM WITH PERCUTANEOUS DEVICE MOVEMENT ALGORITHM

(75) Inventors: Thomas Bromander, Andover, MA (US); David Handler, Newton, MA (US); Tal Wenderow, Newton, MA (US)

(73) Assignee: CORINDUS INC., Waltham, MA (US)

( * ) Notice: Subject to any disclaimer, the term of this patent is extended or adjusted under 35 U.S.C. 154(b) by 0 days.

(21) Appl. No.: 13/444,121

(22) Filed: Apr. 11, 2012

(65) Prior Publication Data

US 2012/0271319 A1      Oct. 25, 2012

Related U.S. Application Data

(63) Continuation of application No. PCT/US2010/052178, filed on Oct. 11, 2010.

(60) Provisional application No. 61/250,739, filed on Oct. 12, 2009.

(51) Int. Cl.
*A61B 19/00* (2006.01)
*G06F 19/00* (2011.01)
*A61M 25/01* (2006.01)

(52) U.S. Cl.
CPC ............ *A61B 19/22* (2013.01); *G06F 19/3437* (2013.01); *A61M 25/01* (2013.01)

(58) Field of Classification Search
CPC ............ A61B 5/15194; A61B 5/15196; A61B 2017/22075; A61B 19/22; A61B 19/2203; A61B 2019/2211; A61B 2019/2215; A61B 2019/2219; A61B 2019/2223; A61B 2019/223; B25J 9/1664; B25J 9/1656; B25J 9/044; G05B 2219/50108; G05B 2219/50109;G05B 2219/50111; G05B 2219/50112; G05B 2219/50113; G05B 19/25; G05B 19/31; G05B 19/37; G05B 19/19; G06F 19/3437; A61M 25/01
USPC .............. 600/407, 424, 426, 434; 606/1, 108, 606/130; 700/245
See application file for complete search history.

(56) References Cited

U.S. PATENT DOCUMENTS

| 2,718,598 A | 9/1955 | Graf |
| 3,147,953 A | 9/1964 | Arth |

(Continued)

FOREIGN PATENT DOCUMENTS

| DE | 2856439 A | 7/1980 |
| DE | 4233323 A | 4/1994 |

(Continued)

OTHER PUBLICATIONS

Anderson, J., Chui, C.K., Cai. Y., Wang Eng, Z.L.M., Eng, X.M.M., Nowinski, W., Solaiyappan, M., Murphy, K., Gailloud, P. & Venbrux, A., Virual Reality Training in International Radiology: The John Hopkins and Kent Ridge Digital Laboratory Experience, Theime Medical Publishers, 2002, 2 pages, vol. 19, No. 2, New York, NY.

(Continued)

*Primary Examiner* — Stephen Holwerda
(74) *Attorney, Agent, or Firm* — Rathe Lindenbaum LLP

(57) ABSTRACT

A workstation configured for operating a robotic catheter system is provided. The workstation includes a user interface configured to receive a user input and a control system operatively coupled to the user interface for remotely and independently controlling movement of at least a first percutaneous device and a second percutaneous device. At least the first percutaneous device is moveable both for advancement and retraction along a longitudinal axis of the first percutaneous device and for rotation about a longitudinal axis of the first percutaneous device. The workstation also includes a device movement algorithm subsystem including at least one set of instructions. The control system controls the first percutaneous device based upon both the user input and the at least one set of instructions of the device movement algorithm subsystem.

30 Claims, 5 Drawing Sheets

(56) References Cited

U.S. PATENT DOCUMENTS

| | | |
|---|---|---|
| 3,308,297 A | 3/1967 | Mansker |
| 4,254,341 A | 3/1981 | Herr et al. |
| 4,382,184 A | 5/1983 | Wernikoff |
| 4,581,538 A | 4/1986 | Lenhart |
| 4,965,456 A | 10/1990 | Huettenrauch et al. |
| 4,977,588 A | 12/1990 | Van Der Ende |
| 5,015,864 A | 5/1991 | Maleki |
| 5,049,147 A | 9/1991 | Danon |
| 5,090,044 A | 2/1992 | Kobayashi |
| 5,133,364 A | 7/1992 | Palermo et al. |
| 5,139,473 A | 8/1992 | Bradshaw et al. |
| 5,185,778 A | 2/1993 | Magram |
| 5,217,003 A * | 6/1993 | Wilk ............... A61B 1/00147 600/109 |
| 5,217,474 A | 6/1993 | Zacca et al. |
| 5,318,541 A | 6/1994 | Viera et al. |
| 5,351,676 A | 10/1994 | Putman |
| 5,377,678 A | 1/1995 | Dumoulin et al. |
| 5,396,880 A | 3/1995 | Kagan et al. |
| 5,423,321 A | 6/1995 | Fontenot |
| 5,425,382 A | 6/1995 | Golden et al. |
| 5,434,775 A | 7/1995 | Sims et al. |
| 5,464,023 A | 11/1995 | Viera |
| 5,484,407 A | 1/1996 | Osypka |
| 5,487,734 A | 1/1996 | Thorne et al. |
| 5,492,131 A | 2/1996 | Galel |
| 5,524,180 A | 6/1996 | Wang et al. |
| 5,540,649 A | 7/1996 | Bonnell et al. |
| 5,578,014 A | 11/1996 | Erez et al. |
| 5,584,078 A | 12/1996 | Saboory |
| 5,586,968 A | 12/1996 | Gruendl et al. |
| 5,623,943 A | 4/1997 | Hackett et al. |
| 5,644,613 A | 7/1997 | Mick |
| 5,654,864 A | 8/1997 | Ritter et al. |
| 5,690,645 A | 11/1997 | Van Erp |
| 5,697,377 A | 12/1997 | Wittkampf |
| 5,704,897 A | 1/1998 | Truppe |
| 5,706,827 A | 1/1998 | Ehr et al. |
| 5,728,044 A | 3/1998 | Shan |
| 5,741,271 A | 4/1998 | Nakao et al. |
| 5,779,623 A | 7/1998 | Bonnell |
| 5,821,920 A | 10/1998 | Rosenberg et al. |
| 5,842,987 A | 12/1998 | Sahadevan |
| 5,851,182 A | 12/1998 | Sahadevan |
| 5,882,333 A | 3/1999 | Schaer et al. |
| 5,957,941 A | 9/1999 | Ream |
| 5,981,964 A | 11/1999 | McAuley et al. |
| 6,004,276 A | 12/1999 | Wright et al. |
| 6,013,038 A | 1/2000 | Pflueger |
| 6,024,749 A | 2/2000 | Shturman et al. |
| 6,048,300 A | 4/2000 | Thornton et al. |
| 6,083,170 A | 7/2000 | Ben-Haim |
| 6,096,004 A | 8/2000 | Meglan et al. |
| 6,126,647 A | 10/2000 | Posey et al. |
| 6,171,234 B1 | 1/2001 | White et al. |
| 6,233,476 B1 | 5/2001 | Strommer et al. |
| 6,258,052 B1 | 7/2001 | Milo |
| 6,261,247 B1 | 7/2001 | Ishikawa et al. |
| 6,266,552 B1 | 7/2001 | Slettenmark |
| 6,285,898 B1 | 9/2001 | Ben-Haim |
| 6,290,675 B1 | 9/2001 | Vujanic et al. |
| 6,351,513 B1 | 2/2002 | Bani-Hashemi et al. |
| 6,358,199 B1 | 3/2002 | Pauker et al. |
| 6,375,471 B1 | 4/2002 | Wendlandt et al. |
| 6,442,451 B1 * | 8/2002 | Lapham ............... B25J 9/1656 318/568.11 |
| 6,447,504 B1 | 9/2002 | Ben-Haim et al. |
| 6,448,571 B1 | 9/2002 | Goldstein |
| 6,497,444 B1 | 12/2002 | Simon |
| 6,499,163 B1 | 12/2002 | Stensby |
| 6,522,909 B1 | 2/2003 | Garibaldi et al. |
| 6,540,670 B1 | 4/2003 | Hirata et al. |
| 6,554,472 B1 | 4/2003 | Dietz et al. |
| 6,610,007 B2 | 8/2003 | Belson et al. |
| 6,653,648 B2 | 11/2003 | Goldstein |
| 6,705,990 B1 | 3/2004 | Gallant et al. |
| 6,726,675 B1 | 4/2004 | Beyar |
| 6,740,103 B2 | 5/2004 | Hall et al. |
| 6,770,066 B1 | 8/2004 | Weaver et al. |
| 6,835,173 B2 | 12/2004 | Couvillon, Jr. |
| 6,878,106 B1 | 4/2005 | Herrmann |
| 6,997,870 B2 | 2/2006 | Couvillon, Jr. |
| 7,087,013 B2 | 8/2006 | Belson et al. |
| 7,112,811 B2 | 9/2006 | Lemer |
| 7,276,044 B2 | 10/2007 | Ferry et al. |
| 7,294,135 B2 | 11/2007 | Stephens et al. |
| 7,608,847 B2 | 10/2009 | Rees |
| 7,615,032 B2 | 11/2009 | Whittaker et al. |
| 7,615,042 B2 | 11/2009 | Beyar et al. |
| 7,632,265 B2 | 12/2009 | Hauck et al. |
| 7,663,128 B2 | 2/2010 | Arterson |
| 7,666,135 B2 | 2/2010 | Couvillon, Jr. |
| 7,686,816 B2 | 3/2010 | Belef et al. |
| 7,697,972 B2 | 4/2010 | Verard et al. |
| 7,706,894 B2 | 4/2010 | Stewart et al. |
| 7,729,743 B2 | 6/2010 | Sabczynski et al. |
| 7,766,894 B2 | 8/2010 | Weitzner et al. |
| 7,769,427 B2 | 8/2010 | Shachar |
| D626,250 S | 10/2010 | Wenderow et al. |
| 7,811,294 B2 | 10/2010 | Strommer et al. |
| 7,848,788 B2 | 12/2010 | Tulley et al. |
| 7,887,549 B2 | 2/2011 | Wenderow et al. |
| 7,905,853 B2 | 3/2011 | Chapman et al. |
| 7,967,773 B2 | 6/2011 | Amborn et al. |
| 7,984,659 B2 | 7/2011 | Fujimoto et al. |
| 8,043,362 B2 | 10/2011 | Gong et al. |
| 8,046,049 B2 | 10/2011 | Govari et al. |
| 8,187,229 B2 | 5/2012 | Weitzner et al. |
| 8,257,302 B2 | 9/2012 | Beyar et al. |
| 8,343,096 B2 | 1/2013 | Kirschenman et al. |
| 8,390,438 B2 | 3/2013 | Olson et al. |
| D680,645 S | 4/2013 | Murphy |
| 2001/0025142 A1 | 9/2001 | Wessels et al. |
| 2002/0087166 A1 | 7/2002 | Brock et al. |
| 2002/0109107 A1 | 8/2002 | Goldstein |
| 2002/0115931 A1 | 8/2002 | Strauss et al. |
| 2002/0168618 A1 | 11/2002 | Anderson et al. |
| 2002/0177789 A1 | 11/2002 | Ferry et al. |
| 2003/0036712 A1 | 2/2003 | Heh et al. |
| 2003/0040671 A1 | 2/2003 | Somogyi et al. |
| 2003/0069719 A1 | 4/2003 | Cunningham et al. |
| 2003/0078003 A1 | 4/2003 | Hunter et al. |
| 2003/0088209 A1 | 5/2003 | Chiu et al. |
| 2003/0176770 A1 | 9/2003 | Merril et al. |
| 2003/0199848 A1 | 10/2003 | Ledesma et al. |
| 2003/0210259 A1 | 11/2003 | Liu et al. |
| 2004/0015974 A1 | 1/2004 | Jeyaraman |
| 2004/0044279 A1 | 3/2004 | Lewin et al. |
| 2004/0064086 A1 | 4/2004 | Gottlieb et al. |
| 2004/0068173 A1 | 4/2004 | Viswanathan |
| 2004/0085294 A1 | 5/2004 | Michelitsch et al. |
| 2004/0113498 A1 | 6/2004 | Kroenke |
| 2004/0138548 A1 | 7/2004 | Strommer et al. |
| 2004/0152974 A1 | 8/2004 | Solomon |
| 2004/0254566 A1 | 12/2004 | Plicchi et al. |
| 2005/0008210 A1 | 1/2005 | Evron et al. |
| 2005/0107697 A1 | 5/2005 | Berke |
| 2005/0119615 A1 | 6/2005 | Noriega et al. |
| 2005/0203382 A1 | 9/2005 | Govari et al. |
| 2005/0222554 A1 | 10/2005 | Wallace et al. |
| 2005/0245846 A1 | 11/2005 | Casey |
| 2005/0256504 A1 | 11/2005 | Long et al. |
| 2005/0273199 A1 | 12/2005 | Ban et al. |
| 2005/0277851 A1 | 12/2005 | Whittaker et al. |
| 2005/0283075 A1 | 12/2005 | Ma et al. |
| 2006/0041181 A1 | 2/2006 | Viswanathan et al. |
| 2006/0041245 A1 | 2/2006 | Ferry et al. |
| 2006/0066574 A1 | 3/2006 | Kim et al. |
| 2006/0074297 A1 * | 4/2006 | Viswanathan ......... A61B 19/22 600/424 |
| 2006/0074442 A1 | 4/2006 | Noriega et al. |
| 2006/0084911 A1 | 4/2006 | Belef et al. |
| 2006/0116575 A1 | 6/2006 | Willis |
| 2006/0146010 A1 | 7/2006 | Schneider |

(56) References Cited

U.S. PATENT DOCUMENTS

| | | | |
|---|---|---|---|
| 2006/0186061 A1 | 8/2006 | Briggs et al. | |
| 2006/0229587 A1 | 10/2006 | Beyar et al. | |
| 2006/0258935 A1 | 11/2006 | Pile-Spellman et al. | |
| 2006/0282140 A1 | 12/2006 | Schock et al. | |
| 2007/0016029 A1 | 1/2007 | Donaldson et al. | |
| 2007/0043338 A1 | 2/2007 | Moll et al. | |
| 2007/0060879 A1 | 3/2007 | Weitzner et al. | |
| 2007/0083111 A1* | 4/2007 | Hossack | A61B 1/00059 600/437 |
| 2007/0083193 A1 | 4/2007 | Werneth et al. | |
| 2007/0103437 A1 | 5/2007 | Rosenberg | |
| 2007/0106247 A1 | 5/2007 | Burnett et al. | |
| 2007/0118079 A1 | 5/2007 | Moberg et al. | |
| 2007/0123070 A1 | 5/2007 | Bencteux | |
| 2007/0137372 A1* | 6/2007 | Devengenzo | A61B 1/00149 74/490.01 |
| 2007/0142749 A1 | 6/2007 | Khatib et al. | |
| 2007/0185480 A1 | 8/2007 | El-Galley et al. | |
| 2007/0185486 A1 | 8/2007 | Hauck et al. | |
| 2007/0197896 A1 | 8/2007 | Moll et al. | |
| 2007/0239106 A1 | 10/2007 | Weitzner et al. | |
| 2007/0250097 A1 | 10/2007 | Weitzner et al. | |
| 2007/0276216 A1 | 11/2007 | Beyar et al. | |
| 2007/0276234 A1 | 11/2007 | Shahidi | |
| 2008/0000485 A1 | 1/2008 | Williams et al. | |
| 2008/0027313 A1 | 1/2008 | Shachar | |
| 2008/0051820 A1 | 2/2008 | Gong et al. | |
| 2008/0059598 A1 | 3/2008 | Garibaldi et al. | |
| 2008/0097224 A1 | 4/2008 | Murphy et al. | |
| 2008/0146922 A1 | 6/2008 | Steins et al. | |
| 2008/0161801 A1 | 7/2008 | Steinke et al. | |
| 2008/0167750 A1 | 7/2008 | Stahler et al. | |
| 2008/0217564 A1* | 9/2008 | Beyar | A61B 6/00 250/515.1 |
| 2008/0221922 A1 | 9/2008 | Putnam et al. | |
| 2008/0221992 A1 | 9/2008 | Bernstein | |
| 2008/0249536 A1 | 10/2008 | Stahler et al. | |
| 2008/0269663 A1 | 10/2008 | Arnold et al. | |
| 2009/0012533 A1 | 1/2009 | Barbagli et al. | |
| 2009/0105639 A1 | 4/2009 | Weitzner et al. | |
| 2009/0110152 A1 | 4/2009 | Manzke et al. | |
| 2009/0131955 A1 | 5/2009 | Wenderow et al. | |
| 2009/0137952 A1 | 5/2009 | Ramamurthy et al. | |
| 2009/0138025 A1 | 5/2009 | Stahler et al. | |
| 2009/0221958 A1 | 9/2009 | Beyar et al. | |
| 2009/0247933 A1 | 10/2009 | Maor et al. | |
| 2009/0247944 A1 | 10/2009 | Kirschenman et al. | |
| 2010/0069833 A1 | 3/2010 | Wenderow et al. | |
| 2010/0073150 A1 | 3/2010 | Olson et al. | |
| 2010/0076308 A1 | 3/2010 | Wenderow et al. | |
| 2010/0076309 A1 | 3/2010 | Wenderow et al. | |
| 2010/0076310 A1 | 3/2010 | Wenderow et al. | |
| 2010/0084586 A1 | 4/2010 | Teodorescu | |
| 2010/0130987 A1 | 5/2010 | Wenderow et al. | |
| 2010/0175701 A1 | 7/2010 | Reis et al. | |
| 2010/0292651 A1 | 11/2010 | Yodfat et al. | |
| 2010/0318100 A1 | 12/2010 | Okamoto et al. | |
| 2011/0004144 A1 | 1/2011 | Beiriger et al. | |
| 2011/0015569 A1 | 1/2011 | Kirschenman et al. | |
| 2011/0109283 A1 | 5/2011 | Kapels et al. | |
| 2011/0144658 A1 | 6/2011 | Wenderow et al. | |
| 2011/0152882 A1 | 6/2011 | Wenderow et al. | |
| 2012/0179032 A1 | 7/2012 | Bromander et al. | |

FOREIGN PATENT DOCUMENTS

| | | | |
|---|---|---|---|
| EP | 0329492 A | 8/1989 | |
| EP | 0331944 A | 9/1989 | |
| EP | 0554986 A | 8/1993 | |
| EP | 0590268 A | 4/1994 | |
| EP | 0970663 A | 1/2000 | |
| EP | 1415660 A | 5/2004 | |
| EP | 1442720 A | 8/2004 | |
| EP | 1504713 A | 2/2005 | |
| EP | 1554986 A | 7/2005 | |
| EP | 1792638 A | 6/2007 | |
| FR | 2167098 A | 8/1973 | |
| JP | 07184923 | 7/1995 | |
| JP | 7328016 | 12/1995 | |
| SU | 279814 A | 7/1975 | |
| SU | 992067 A | 1/1983 | |
| WO | 9320876 A | 10/1993 | |
| WO | 9502233 A | 1/1995 | |
| WO | 9621486 A | 7/1996 | |
| WO | 0174252 | 10/2001 | |
| WO | 0209571 A | 2/2002 | |
| WO | 02064011 A | 8/2002 | |
| WO | 2005000105 A | 1/2005 | |
| WO | 2006018841 A | 2/2006 | |
| WO | 2006120666 A | 11/2006 | |
| WO | 2007036925 A | 4/2007 | |
| WO | 2009137410 A | 11/2009 | |
| WO | 2010025336 A | 3/2010 | |
| WO | 2010025338 A | 3/2010 | |
| WO | 2010068783 A | 6/2010 | |
| WO | 2010107916 A | 9/2010 | |
| WO | 2011046874 A | 4/2011 | |

OTHER PUBLICATIONS

Becker, Y, Cancer in ataxia-telangiectasia patients: Analysis of factors leading to radiation-induced and spontaneous tumors, Anticancer Res., 1986, vol. 6, No. 5, Abstract, pp. 1021-1032, Israel.

Beyar, R., Gruberg, L., Deleanu, D., Roguin, A., Almagor, Y., Cohen, S., Kumar, G., & Wenderow, T., Remote Control Percutaneous Coronary Interventions, Journal of American College of Cardiology, 2006, vol. 47, No. 2, 5 pages, Elsevier Inc., Haifa, Israel.

Biazzi, L. & Garbagna, P., Exposition Aux Radiations Et Protection Pendant Les Examens Angiographiques, Ann. Radiol., 1979, vol. 22, No. 4, Abstract, pp. 345-347, France.

Essinger A., Raimondi, S. & Valley, J.F., Radiation Exposure to the Examiner During Coronary Angiography, Ann. Radiol., 1979 vol. 22 No. 4 Abstract, pp. 340-343, France.

Favaretti, C., Stritoni, P., Mariotti, A., Bressan, M. & Razzolini, R., The Distribution and Activities of Hemodynamic Laboratories in Italy: The implications for the Quality of Services, G Ital Cardiol, May 1994, vol. 24 No. 5, Abstract, pp. 477-482, Italy.

Magnavita, N. & Fileni, A., Occupational risk caused by ultrasound in medicine, Radiologica Medica, Jul.-Aug. 1994, vol. 88, No. 1-2, Abstract, pp. 107-111, Italy.

Roach, H., Larson, E., Cobran, T. & Bartlett, B., Intravenous site care practices in critical care: a national survey, Heart Lung, Sep.-Oct. 1995, vol. 24, No. 5, Abstract, pp. 420-424, Washington D.C., United States.

Van Den Brand, M., Utilization or coronary angioplasty and cost or angioplasty disposables in 14 western European countries, Europe Heart Journal, Mar. 1993, vol. 14, No. 3, Abstract, pp. 391-397, Rotterdam, Netherlands.

Wu, J.R., Huang, T.Y., Wu, D.K., Hsu, P.C. & Weng, P.S., An investigation of radiation exposure on pediatric patients and doctors during cardiac catheterization and cineangiography, Journal of Medical Sciences, Sep. 1991, vol. 7, No. 9, Abstract, pp. 448-453, Taiwan, China.

* cited by examiner

CATHETER SYSTEM WITH PERCUTANEOUS DEVICE MOVEMENT ALGORITHM

CROSS-REFERENCE TO RELATED PATENT APPLICATION

This application is a continuation of International Application No. PCT/US2010/052178, filed Oct. 11, 2010, which claims the benefit of U.S. Provisional Application No. 61/250,739 filed Oct. 12, 2009 both of which are incorporated herein by reference in their entirety.

BACKGROUND OF THE INVENTION

The present invention relates generally to the field of catheter systems for performing diagnostic and/or intervention procedures. The present invention relates specifically to catheter systems including a controller including one or more algorithms or instruction sets for controlling the movement of a percutaneous device.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than some other types of procedures. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases (e.g., hypertension, etc.) may be treated using catheterization procedures.

SUMMARY OF THE INVENTION

One embodiment of the present invention relates to a workstation configured for operating a robotic catheter system. The workstation includes a user interface configured to receive a user input and a control system operatively coupled to the user interface for remotely and independently controlling movement of at least a first percutaneous device and a second percutaneous device. At least the first percutaneous device is moveable both for advancement and retraction along a longitudinal axis of the first percutaneous device and for rotation about a longitudinal axis of the first percutaneous device. The workstation also includes a device movement algorithm subsystem including at least one set of instructions. The control system controls the first percutaneous device based upon both the user input and the at least one set of instructions of the device movement algorithm subsystem.

Another embodiment of the present invention relates to a catheter procedure system. The catheter procedure system includes a bedside system and a remote workstation. The bedside system includes a first percutaneous device actuating mechanism including an axial movement actuator for moving the first percutaneous device along a longitudinal axis of the first percutaneous device and a rotation actuator for rotating the first percutaneous device about a longitudinal axis of the first percutaneous device. The bedside system also includes a second percutaneous device actuating mechanism. The remote workstation includes a user interface configured to receive a user input and a control system operatively coupled to the user interface and to the bedside system for remotely and independently controlling movement of the first percutaneous device and the second percutaneous device. The workstation also includes a device movement algorithm subsystem including at least one set of instructions. The control system controls the first percutaneous device based upon both the user input and the at least one set of instructions of the device movement algorithm subsystem.

Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
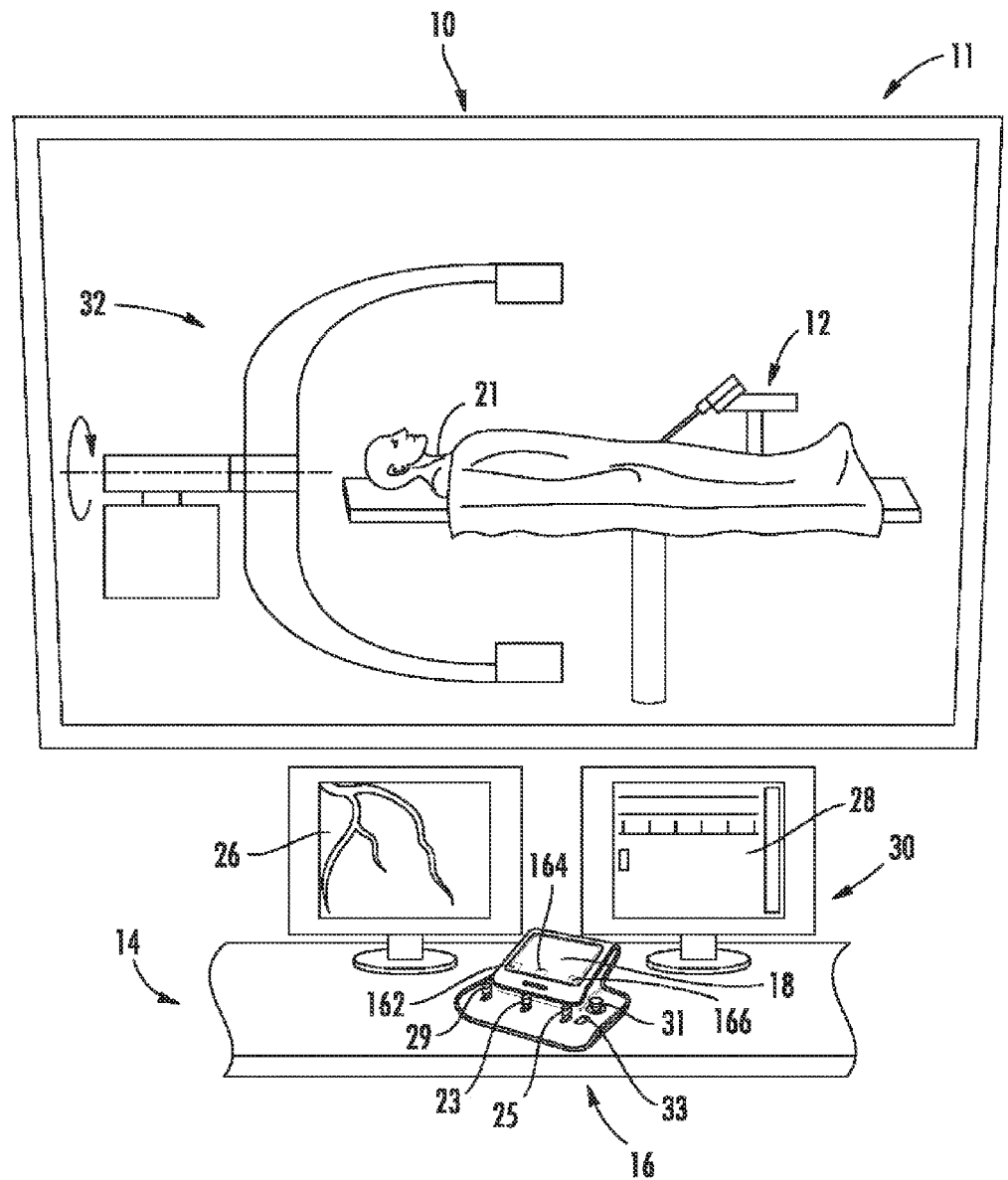
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., balloon angioplasty, stent placement, treatment of peripheral vascular disease, etc.) during which a catheter is used to treat a disease. It should be noted, however, that one skilled in the art would recognize that, certain specific percutaneous intervention devices or components (e.g., type of guide wire, type of catheter, etc.) will be selected based on the type of procedure that is to be preformed. Catheter procedure system 10 is capable of performing any number of catheter based medical procedures with minor adjustments to accommodate the specific percutaneous devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure. For example, catheter procedure system 10 may be used for the treatment of hypertension utilizing a radiofrequency emitting catheter to deactivate certain nerves that enervate the kidneys to control hypertension.

Catheter procedure system 10 includes lab unit 11 and workstation 14. Catheter procedure system 10 includes a robotic catheter system, shown as bedside system 12, located within lab unit 11 adjacent patient 21. Generally, bedside system 12 may be equipped with the appropriate percutaneous devices (e.g., guide wires, guide catheters, working catheters, catheter balloons, stents, diagnostic catheters, etc.) or other components (e.g., contrast media, medicine, etc.) to allow the user to perform a catheter based medical procedure. A robotic catheter system, such as bedside system 12, may be any system configured to allow a user to perform a catheter-based medical procedure via a robotic system by operating various controls such as the controls located at workstation 14. Bedside system 12 may include any number and/or combination of components to provide bedside system 12 with the functionality described herein. Various embodiments of bedside system 12 are described in detail in P.C.T. International Application No. PCT/US2009/042720, filed May 4, 2009, which is incorporated herein by reference in its entirety.

In one embodiment, bedside system 12 may be equipped to perform a catheter based diagnostic procedure. In this embodiment, bedside system 12 may be equipped with one or more of a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart.

In another embodiment, bedside system 12 may be equipped to perform a catheter based therapeutic procedure. In this embodiment, bedside system 12 may be equipped with a guide catheter, a guide wire, and a working catheter (e.g., a balloon catheter, a stent delivery catheter, ablation catheter, etc.). In one embodiment, bedside system 12 may equipped with a working catheter that includes a secondary lumen that is threaded over the guide wire during a procedure. In another embodiment, bedside system 12 may be equipped with an over-the-wire working catheter that includes a central lumen that is threaded over the guide wire during a procedure. In another embodiment, bedside system 12 may be equipped with an intravascular ultrasound (IVUS) catheter. In another embodiment, any of the percutaneous devices of bedside system 12 may be equipped with positional sensors that indicate the position of the component within the body.

Bedside system 12 is in communication with workstation 14, allowing signals generated by the user inputs and/or control system of workstation 14 to be transmitted to bedside system 12 to control the various functions of beside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30. User interface 30 includes controls 16. Controls 16 allow the user to control bedside system 12 to perform a catheter based medical procedure. For example, controls 16 may be configured to cause bedside system 12 to perform various tasks using the various percutaneous devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure, etc.). In some embodiments, one or more of the percutaneous intervention devices may be steerable, and controls 16 may be configured to allow a user to steer one or more steerable percutaneous device. In one such embodiment, bedside system 12 may be equipped with a steerable guide catheter, and controls 16 may also be configured to allow the user located at remote workstation 14 to control the bending of the distal tip of a steerable guide catheter. Further embodiments of catheter system 10 including a steerable guide catheter are disclosed in P.C.T. International Application No. PCT/US2010/27666, filed Mar. 17, 2010, which is incorporated herein by reference in its entirety.

In one embodiment, controls 16 include a touch screen 18, a dedicated guide catheter control 29, a dedicated guide wire control 23, and a dedicated working catheter control 25. In this embodiment, guide wire control 23 is a joystick configured to advance, retract, or rotate a guide wire, working catheter control 25 is a joystick configured to advance, retract, or rotate a working catheter, and guide catheter control 29 is a joystick configured to advance, retract, or rotate a guide catheter. In addition, touch screen 18 may display one or more icons (such as icons 162, 164, and 166) that control movement of one or more percutaneous devices via bedside system 12 or to receive various inputs from the user as discussed below. Controls 16 may also include a balloon or stent control that is configured to inflate or deflate a balloon and/or a stent. Each of the controls may include one or more buttons, joysticks, touch screens, etc., that may be desirable to control the particular component to which the control is dedicated. As discussed in more detail below, catheter procedure system 10 includes a percutaneous device movement algorithm module or movement instruction module 114 that dictates how bedside system 12 responds to a user's manipulation of controls 16 to cause a percutaneous device to move in a particular way.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 26 and second monitor 28 may be configured to display procedure specific information (e.g., duration of procedure, catheter or guide wire position, volume of medicine or contrast agent delivered, etc.). In one embodiment, the user may interact with or select various icons or information displayed on monitors 26 and 28 using a user input device or control (e.g., a mouse). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MRI, ultrasound, etc.). In an exemplary embodiment, imaging system 32 is a digital x-ray imaging device that is in communication with workstation 14. As shown in FIG. 1, imaging system 32 may include a C-arm that allows imaging system 32 to partially or completely rotate around patient 21 in order to obtain images at different angular positions relative to patient 21 (e.g., sagital views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, working catheter, stent, etc. during the procedure. The image or images may be displayed on first monitor 26 and/or second monitor 28.

In addition, the user of workstation 14 may be able to control the angular position of imaging system 32 relative to the patient to obtain and display various views of the patient's heart on first monitor 26 and/or second monitor 28. Displaying different views at different portions of the procedure may aid the user of workstation 14 properly move and position the percutaneous devices within the 3D geometry of the patient's heart. For example, displaying the proper view during a procedure may allow the user to view a patient's vascular system from the proper angle to ensure that the distal tip of a steerable guide catheter is bent in the proper way to ensure the catheter is moved as intended. In addition, displaying different views at different portions of a procedure may aid the user in selecting the appropriate instruction set of movement instruction module 114 discussed below. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 16 may also be configured to allow the user positioned at workstation 14 to control various functions of imaging system 32 (e.g., image capture, magnification, collimation, c-arm positioning, etc.).

Figure 2:
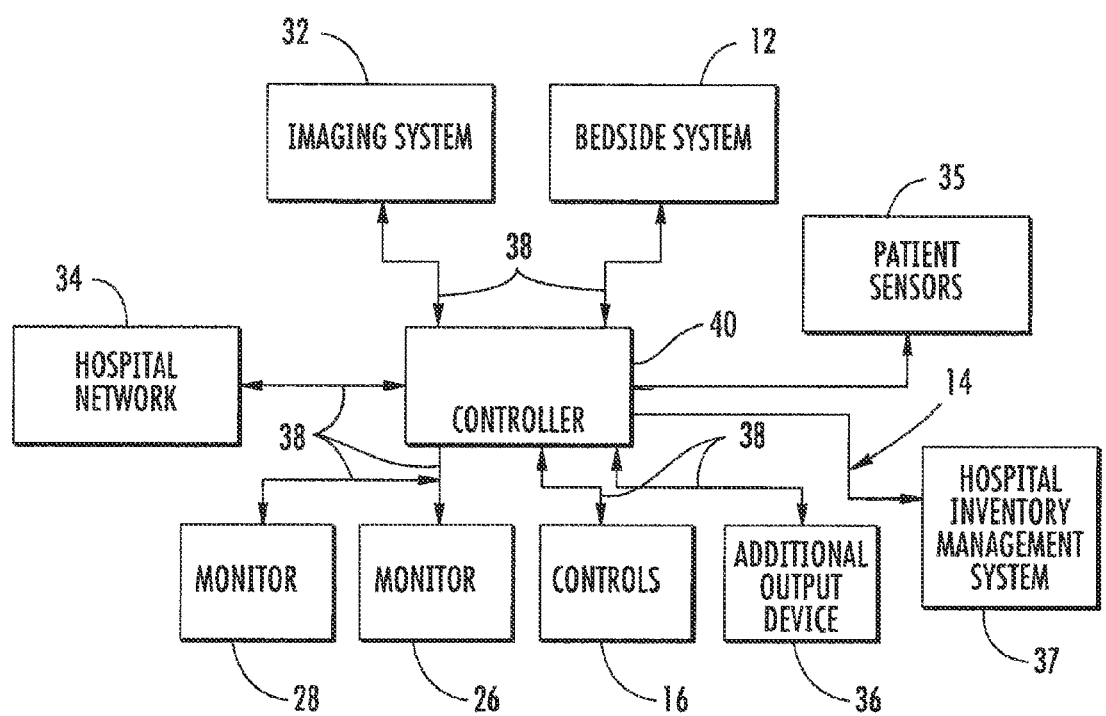
FIG. 2 is a block diagram of a catheter procedure system according to an exemplary embodiment.

Referring to FIG. 2, a block diagram of catheter procedure system 10 is shown according to an exemplary embodiment. Catheter procedure system 10 may include a control system, shown as controller 40. As shown in FIG. 2, controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34, one or more additional output devices 36 (e.g., printer, disk drive, cd/dvd writer, etc.), and a hospital inventory management system 37.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, contrast media and/or medicine injection systems, medicine tracking and/or logging systems, user logs, encryption systems, systems to restrict access or use of catheter procedure system 10, robotic catheter systems of the past, present, or future, etc. Further embodiments of catheter procedure system 10 including inflation and/or contrast media injection systems are disclosed in P.C.T. International Application No. PCT/US2009/67540, filed Dec. 10, 2009, which is incorporated herein by reference in its entirety.

Figure 3:
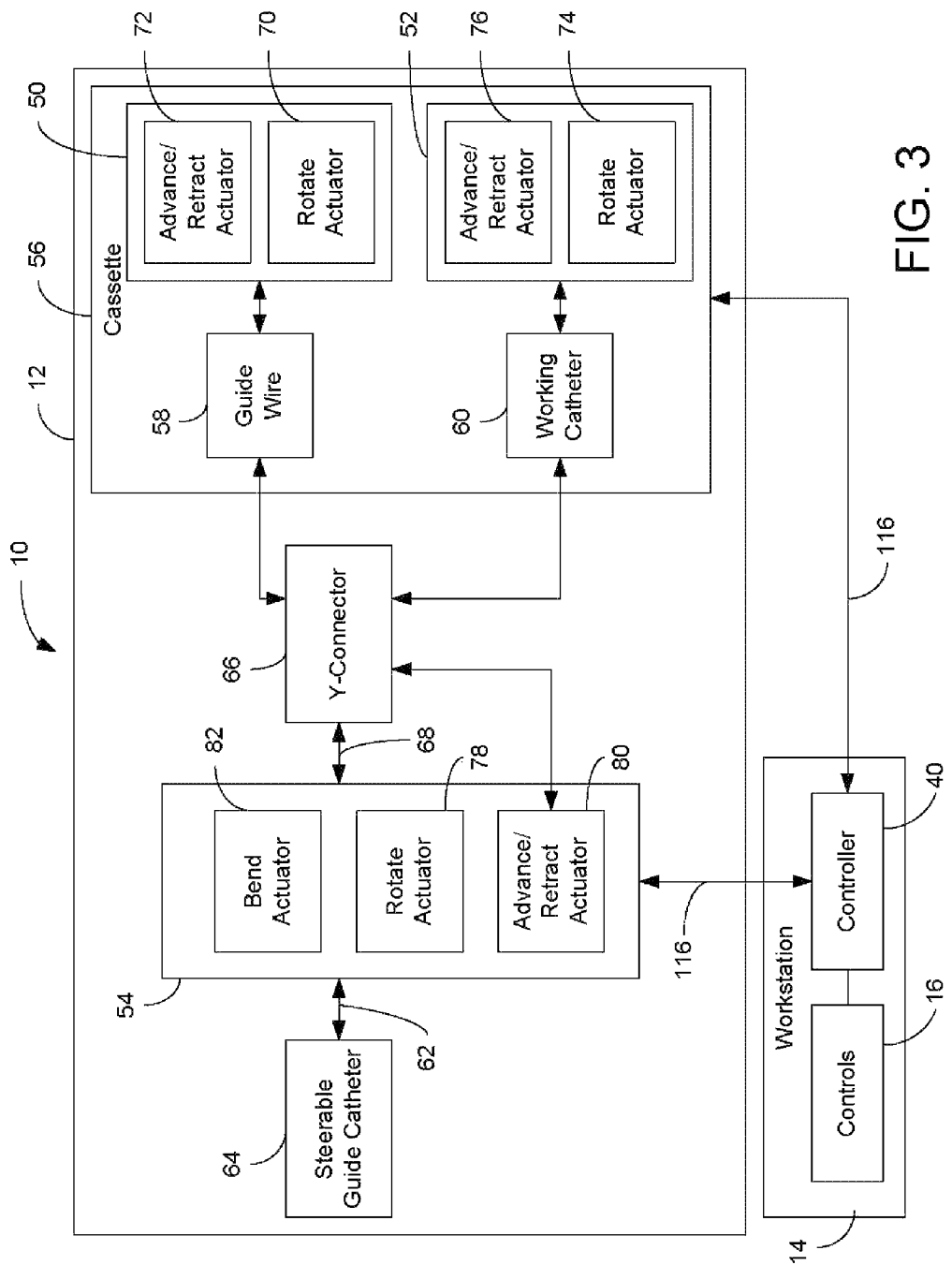
FIG. 3 is a block diagram of a catheter procedure system depicting various actuating mechanisms according to an exemplary embodiment.

Referring to FIG. 3, a block diagram of an embodiment of catheter procedure system 10 is shown according to an exemplary embodiment. Catheter procedure system 10 may include various actuating mechanisms that move an associated percutaneous device in response to a user's manipulation of controls 16. In the embodiment shown, catheter procedure system 10 includes a guide wire actuating mechanism 50, a working catheter actuating mechanism 52, and a guide catheter actuating mechanism 54. In other embodiments, catheter procedure system 10 may include an actuating mechanism for inflating an angioplasty or stent delivery balloon and an actuating mechanism for delivering contrast agent. In the embodiment shown, guide wire actuating mechanism 50 and working catheter actuating mechanism 52 are incorporated within cassette 56 which is coupled to a base of bedside system 12. Additional embodiments of bedside system 12 and cassette 56 are described in detail in P.C.T. International Application No. PCT/US2009/042720, filed May 4, 2009, which is incorporated herein by reference in its entirety. Further embodiments of catheter procedure system 10 are described in detail in P.C.T. International Application No. PCT/US2010/27666, filed Mar. 17, 2010, and in P.C.T. International Application No. PCT/US2009/67540, filed Dec. 10, 2009, both of which are incorporated herein by reference in their entireties.

Guide wire actuating mechanism 50 is coupled to guide wire 58 such that guide wire actuating mechanism 50 is able to cause guide wire 58 to advance, retract, and rotate. Working catheter actuating mechanism 52 is coupled to working catheter 60 such that working catheter actuating mechanism 52 is able to cause working catheter 60 to advance, retract, and rotate. Connector 62 couples guide catheter 64 to guide catheter actuating mechanism 54 such that guide catheter actuating mechanism 54 is able to cause guide catheter 64 to advance, retract, and rotate. In various embodiments, guide wire actuating mechanism 50, working catheter actuating mechanism 52, and guide catheter actuating mechanism may each include an engagement structure (e.g., one or more pairs of pinch wheels) suitable for engaging the respective percutaneous device such that the actuating mechanism is able to impart axial and/or rotational movement to the percutaneous device.

A Y-connector 66 is coupled to guide catheter actuating mechanism 54 via connector 68. In various embodiments, connector 68 may be a component separate from both Y-connector 66 and guide catheter actuating mechanism 54. In other embodiments, connector 68 may be part of (e.g., integral with) Y-connector 66 or part of actuating mechanism 54. In the embodiment shown, Y-connector 66 is also connected to cassette 56.

In one embodiment, Y-connector 66 includes a first leg, a second leg, and a third leg. The first leg of the Y-connector is connected to or in communication with the internal lumen of guide catheter 64. The second leg is angled away from the longitudinal axis of guide catheter 64. The second leg provides a port for the injection of fluids (e.g., contrast media, medicine, etc.) into the lumen of guide catheter 64. The third leg of Y-connector 66 is coupled to a cassette 56 and receives both guide wire 58 and working catheter 60. Thus, by this arrangement, guide wire 58 and working catheter 60 are inserted through Y-connector 66 into the internal lumen of guide catheter 64.

Guide wire actuating mechanism 50 includes a rotate actuator 70 and an advance/retract actuator 72. Rotate actuator 70 is configured to cause rotation of guide wire 58 about its longitudinal axis. Advance/retract actuator 72 is configured to advance and/or retract guide wire 58 (i.e., to advance and/or retract along the longitudinal axis of the guide wire) within patient 21. Working catheter actuating mechanism 52 includes a rotate actuator 74 and an advance/retract actuator 76. Rotate actuator 74 is configured to cause rotation of working catheter 60 about its longitudinal axis. Advance/retract actuator 76 is configured to advance and/or retract working catheter 60 (i.e., to advance and/or retract along the longitudinal axis of the working catheter) within patient 21. Guide catheter actuating mechanism 54 includes a rotate actuator 78, an advance/retract actuator 80, and a bend actuator 82. Rotate actuator 78 is configured to cause rotation of guide catheter 64 about its longitudinal axis. Advance/retract actuator 80 is configured to advance and/or retract guide catheter 64 (i.e., to advance and/or retract along the longitudinal axis of the guide catheter) within patient 21. In some embodiments, guide catheter 64 may include one or more bend control elements that allow the user to cause bending of the distal tip of guide catheter 64. In such an embodiment, bend actuator 82 causes the distal tip of guide catheter 64 to bend in response to a user's manipulation of controls 16.

As shown in the block diagram of FIG. 3, controls 16 and controller 40 located at workstation 14 are communicably coupled to various portions of bedside system 12 to allow the user and/or control system to control movement of guide wire 58, working catheter 60 and guide catheter 64 and any other percutaneous devices that bedside system 12 is equipped with. In the embodiment shown, controls 16 and controller 40 are coupled to guide catheter actuating mechanism 54 to allow the user to move guide catheter 64. In addition, controls 16 and controller 40 are coupled to cassette 56 to allow the user to control guide wire 58 via guide wire actuating mechanism 50 and to control working catheter 60 via working catheter actuating mechanism 52. Control signals 116 generated by the controls and controller at workstation 14 are communicated to bedside system 12 to control movement of percutaneous devices discussed herein.

Figure 4:
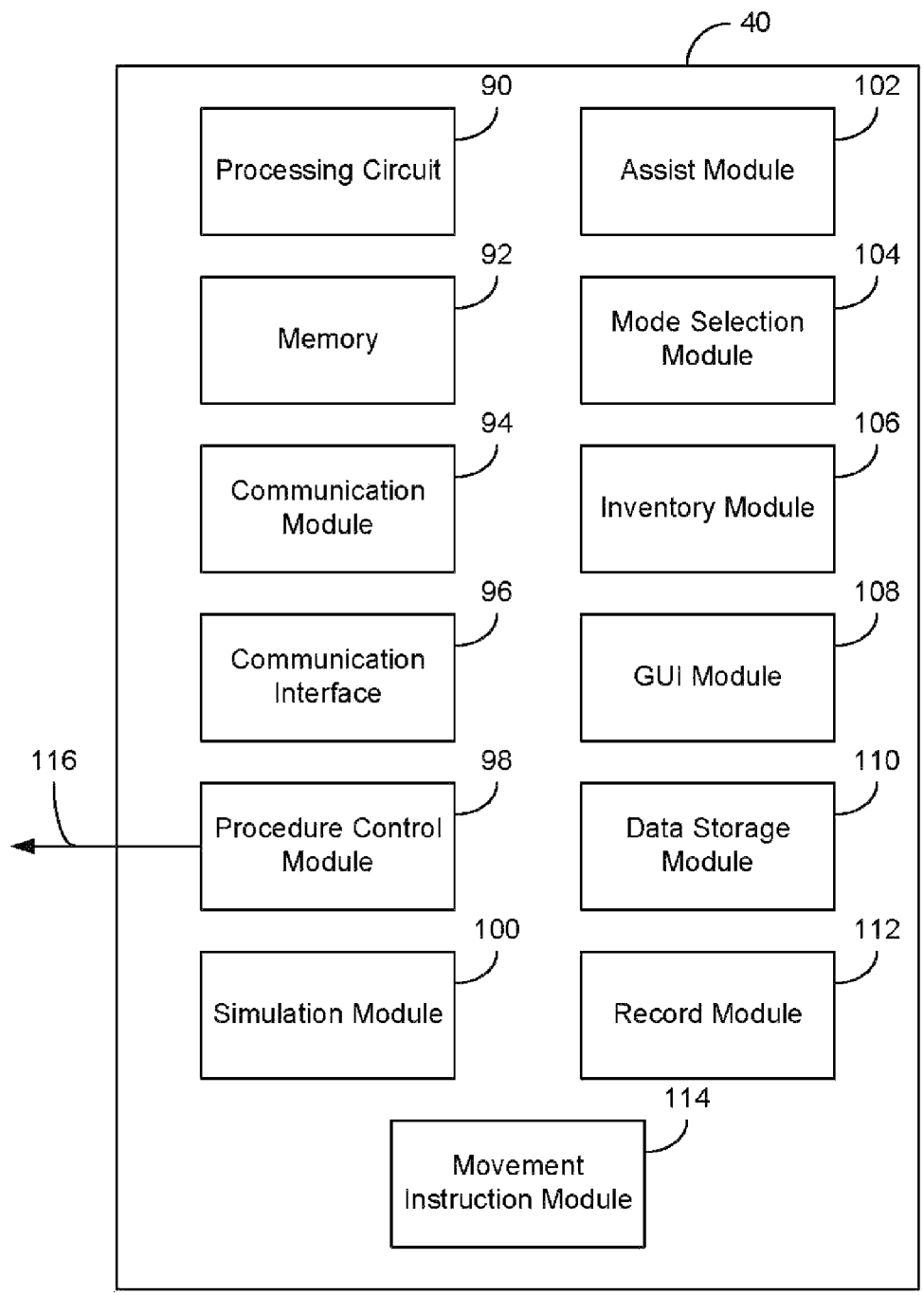
FIG. 4 is a block diagram of a controller for controlling a robotic catheter system according to an exemplary embodiment.

Referring to FIG. 4, a block diagram of controller 40 is shown according to an exemplary embodiment. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 90, memory 92, communication module or subsystem 94, communication interface 96, procedure control module or subsystem 98, simulation module or subsystem 100, assist control module or subsystem 102, mode selection module or subsystem 104, inventory module or subsystem 106, GUI module or subsystem 108, data storage module or subsystem 110, and record module or subsystem 112.

Processing circuit 90 may be a general purpose processor, an application specific processor (ASIC), a circuit containing one or more processing components, a group of distributed processing components, a group of distributed computers configured for processing, etc., configured provide the functionality of module or subsystem components 94, 98-114. Memory 92 (e.g., memory unit, memory device, storage device, etc.) may be one or more devices for storing data and/or computer code for completing and/or facilitating the various processes described in the present disclosure. Memory 92 may include volatile memory and/or non-volatile memory. Memory 92 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 92 is communicably connected to processing circuit 90 and module components 94, 98-114 (e.g., via a circuit or any other wired, wireless, or network connection) and includes computer code for executing one or more processes described herein. A single memory unit may include a variety of individual memory devices, chips, disks, and/or other storage structures or systems.

Module or subsystem components 94, 98-114 may be computer code (e.g., object code, program code, compiled code, script code, executable code, or any combination thereof), hardware, software, or any combination thereof, for conducting each module's respective functions. Module components 94, 98-114 may be stored in memory 92, or in one or more local, distributed, and/or remote memory units configured to be in communication with processing circuit 90 or another suitable processing system.

Communication interface 96 includes one or more component for communicably coupling controller 40 to the other components of catheter procedure system 10 via communication links 38. Communication interface 96 may include one or more jacks or other hardware for physically coupling communication links 38 to controller 40, an analog to digital converter, a digital to analog converter, signal processing circuitry, and/or other suitable components. Communication interface 96 may include hardware configured to connect controller 40 with the other components of catheter procedure system 10 via wireless connections. Communication module 94 is configured to support the communication activities of controller 40 (e.g., negotiating connections, communication via standard or proprietary protocols, etc.).

Data storage module 110 is configured to support the storage and retrieval of information by controller 40. In one embodiment, data storage module 110 is a database for storing patient specific data, including image data. In another embodiment, data storage module 110 may be located on hospital network 34. Data storage module 110 and/or communication module 94 may also be configured to import and/or export patient specific data from hospital network 34 for use by controller 40.

Controller 40 also includes a procedure control module 98 configured to support the control of bedside system 12 during a catheter based medical procedure. Procedure control module 98 allows the user to operate bedside system 12 by manipulating controls 16. To provide this control, procedure control module 98 is in communication with a percutaneous device movement algorithm or movement instruction module 114. Movement instruction module 114 includes one or more movement algorithms or instruction sets (e.g., a library of instruction sets) that dictate how bedside system 12 operates in response to a user's manipulation of controls 16 to produce movement of one or more of the percutaneous devices (e.g., guide wire, working catheter, guide catheter, etc.) that bedside system 12 is equipped with. In various embodiments, procedure control module 98 is configured to generate one or more control signals 116 based upon the user's manipulation of controls 16 and based upon one or more active set of movement instructions provided by movement instruction module 114. Control signals generated by procedure control module 98 are communicated from controller 40 to the appropriate actuator or actuators of bedside system 12. The control signals control the appropriate actuators to cause movement of a percutaneous device in accordance with the manipulation of controls 16 by the user and with the active instruction set of movement instruction module 114. In this manner, movement of the percutaneous device may be controlled from workstation 14. Procedure control module 98 may also cause data appropriate for a particular procedure to be displayed on monitors 26 and 28. Procedure control module 98 may also cause various icons (e.g., icons 162, 164, 166, etc.) to be displayed on touch screen 18 that the user may interact with to control the use of bedside system 12.

Figure 5:
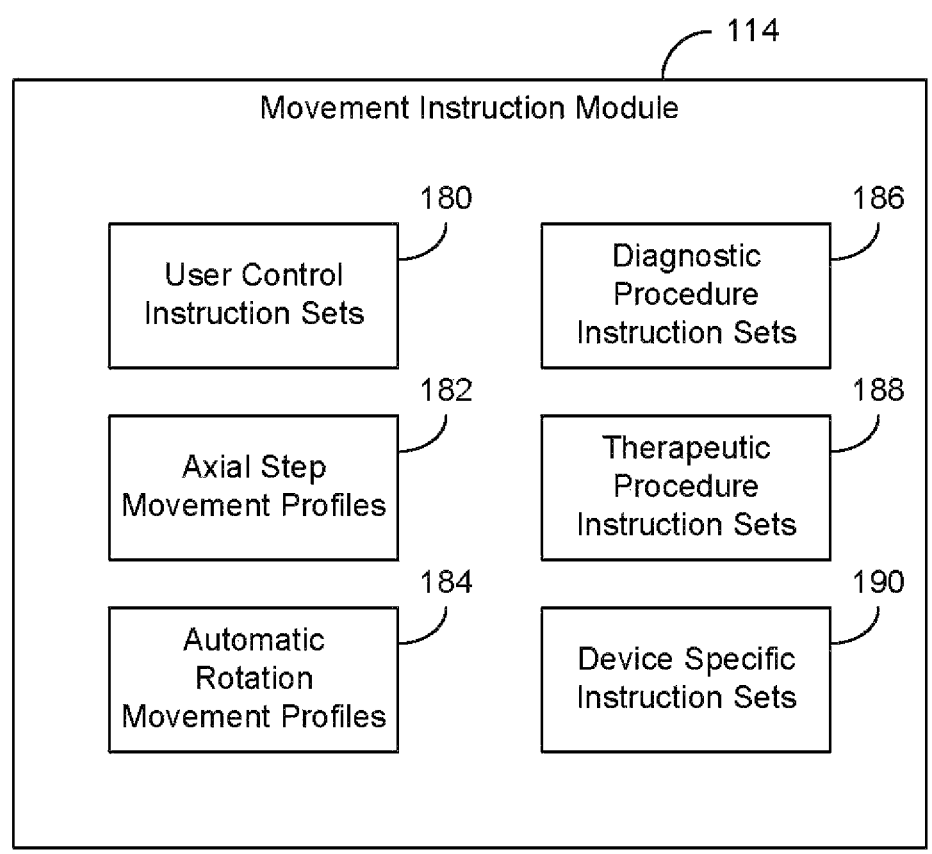
FIG. 5 is a block diagram of a movement instruction module according to an exemplary embodiment.

Referring to FIG. 5, movement instruction module 114 is depicted according to an exemplary embodiment. In one embodiment, movement instruction module 114 is configured to allow the user to specifically control each movement of a percutaneous device via bedside system 12. In this embodiment, movement instruction module 114 includes a user control instruction set 180 that includes device movement instructions to cause bedside system 12 to move (e.g., advance, retract, rotate, etc.) the percutaneous device in a predefined, set manner (e.g., at a set rate, in a set direction, etc.) in response to a particular input received by controls 16.

For example, user control instruction set 180 of movement instruction module 114 may be configured such that when guide wire control 23 is actuated, bedside system 12 causes the guide wire to advance, retract or rotate at a set rate. Thus, in this embodiment, movement instruction module 114 is configured to allow the user to control the rate and direction of movement of a percutaneous device based on the user's interaction with controls 16. Thus, for certain procedures, the user may select or activate user control instruction set 180 when the user desires to directly control every movement of the percutaneous device by manipulating controls 16.

In one specific embodiment, the movement rate of a percutaneous device caused by bedside system 12 is proportional to the amount of displacement of the control. For example, where controls 23, 25 and 29 are joystick controls, user control instruction set 180 may be configured such that the movement rate of a percutaneous device caused by bedside system 12 is proportional to the degree of displacement of the joystick from the resting position. Further, in this embodiment, the direction of movement (e.g., advancement or retraction) of the percutaneous device caused by bedside system 12 is based on the direction of displacement of the joystick from the resting position.

As discussed above, controls 16 may include a multiplier button 33. Movement instruction module 114 may include a first set of instructions that is active or operative when multiplier button 33 is not activated and a second set of instructions that is operative when multiplier button 33 is activated. In this embodiment, the second set of instructions is configured to cause a percutaneous device to be moved faster by bedside system 12 than it would be moved under the control of the first set of instructions. Thus, when the user presses multiplier button 33, the second set of instructions of movement instruction module 114 is activated causing an increase in the rate of movement of a percutaneous device that results from a particular operation of controls 16. For example, if the first set of instructions of movement instruction module 114 dictates a 1 mm per second rate of advancement of the working catheter when control 16 is fully actuated (e.g., full displacement of a joystick control), then the second set of instructions of movement instruction module 114 may cause a 2 mm per second rate of advancement of the working catheter when control 16 is fully actuated.

In various embodiments, movement instruction module 114 may include various sets of instructions to facilitate the performance of certain movements of percutaneous devices via bedside system 12 without the user having to manually manipulate controls 16 in a series of complicated movements to generate a particular type of movement by the percutaneous device. In these embodiments, a user may select or activate a particular movement instruction set that defines a movement profile, and when controls 16 are manipulated by the user, the percutaneous device is moved in accordance with the movement profile. Thus, movement instruction module 114 may allow a particular movement of a percutaneous device associated with the activated instruction set to be performed consistently in each procedure. The movement profile needed to perform a particular procedure may depend on factors such as, the type of condition being treated (e.g., a chronic total occlusion (CTO), partial occlusion, etc.), the location of the condition being treated (e.g., coronary arteries, peripheral arteries, etc.), the geometry of the area being treated, the particular type (e.g., make, model, size, etc.) of percutaneous device being used, etc.

In one embodiment, movement instruction module 114 may include an axial step movement profile instruction set 182 that is configured to cause bedside system 12 to move a percutaneous device in series of small axially steps or pulses when a user operates controls 16 to cause advancement of the percutaneous device. In such an embodiment, axial step movement profile instruction set 182 of movement instruction module 114 may specify a step distance (i.e., a distance parameter of the step, e.g., 0.2 mm, 0.4 mm, 0.8 mm, 1 mm, 1.5 mm, 2 mm, etc.), a step duration (i.e., the length of time it takes the device to move the step distance, e.g., 0.05 sec, 0.1 sec, 0.3 sec, 0.5, sec, 1 sec, etc.), and a rest duration (i.e., the length of time between steps, e.g., 0.05 sec, 0.1 sec, 0.3 sec, 0.5, sec, 1 sec, etc.). Such pulsed movement may be used to allow a percutaneous device to traverse a CTO. In this embodiment, advancement of the percutaneous device along its longitudinal axis occurs in a series of pulsed axial steps defined by the step distance, step duration, and rest duration.

In another embodiment, axial step movement profile instruction set 182 of movement instruction module 114 may include a movement profile that is configured to cause bedside system 12 to intersperse one or more retract pulses (i.e., pulses the move the device in a direction opposite of the direction of advancement) with the axial advance pulses when a user operates controls 16 to cause net advancement of a percutaneous device. In one embodiment, movement instruction module 114 may be configured to cause bedside system 12 to move a percutaneous device in a set of forward pulses that is followed by one or more retract pulses, which is then followed by a second set of forward pulses, and so on, while the user operates controls 16 to cause advancement of the percutaneous device. To ensure net forward progress utilizing such a movement profile, the instruction set ensures that the distance traveled during each set of forward pulses is greater than the distance traveled during the retract pulses. The retract pulse may allow the percutaneous device to disengage from a structure (e.g., lesion, vessel wall, etc.) prior to further advancement. In various embodiments, movement instruction module 114 may be configured to cause pulsed movement of any percutaneous device with which bedside system 12 is equipped, including the guide wire, working catheter, and guide catheter.

In another embodiment, movement instruction module 114 may include an automatic rotation movement profile instruction set 184 that is configured to cause bedside system 12 to rotate the percutaneous device at a set rate as the percutaneous device is advanced and/or retracted in response to the user's operation of controls 16 to cause advancement/retraction of a percutaneous device. In such an embodiment, automatic rotation movement profile instruction set 184 of movement instruction module 114 may specify an amount of rotation experienced by the percutaneous device as the percutaneous device is advanced or retracted (i.e., a rotation rate). The rotation rate may be specified in terms of degrees of rotation per unit of axial distance traveled (e.g., 360 degrees of rotation for each 2 mm traveled, etc.) or may be specified in terms of degrees of rotation per unit of time of axial travel (e.g., 360 degrees of rotation for each 5 seconds of axial travel). This embodiment allows the user to perform a drilling or corkscrew action with the percutaneous device without having to manually operate controls 16 to cause both axial movement and rotation. In various embodiments, movement instruction module 114 may include instructions to cause such movement of any device with which bedside system 12 is equipped, including the guide wire, working catheter, and guide catheter.

In various embodiments, controller 40 is configured to allow a user to set or select one more of the parameters associated with a particular movement profile. For example, a user may input or select the desired step distance, step duration, rest duration, rotation rate, etc., for the movement profiles discussed above. In these embodiments, controls 16 may include at least one user input device or a control (e.g., touch screen icons 162, 164, 166, keyboard, etc.) that allows the user to input the parameters associated with a movement profile.

In one embodiment, one or more user input devices of controls 16 may be a dedicated user input device that is associated with one of the movement instruction sets of movement instruction module 114 such that operation of the associated user input device itself causes bedside system 12 to move the percutaneous device in accordance with the movement profile. In one embodiment, procedure control module 98 may be configured to display one or more icons (e.g., icons 162, 164, 166, etc.) on touch screen 18 that is associated with a set of movement instructions (e.g., profiles 182 and 184). When the user operates or touches one of the touch screen icons associated with a movement instruction set, bedside system 12 is controlled to move a percutaneous device in accordance with the instruction set associated with the touch screen icon. In one embodiment, certain user input devices of controls 16 (e.g., one or more joysticks) may allow for total or specific control of movement of the percutaneous device by the user, and manipulation of the dedicated touch screen icon causes bedside system to advance the percutaneous device in accordance with an associated axial step movement profile or rotation movement profile.

In one embodiment, bedside system 12 may be equipped with a steerable guide catheter 64 that may be steered by bending the distal tip via bend actuator 82 in response to a user's manipulation of controls 16. In this embodiment, the distal tip of steerable guide catheter 64 may be bent to a particular shape or angle to position guide catheter 64 properly to perform a particular procedure, and movement instruction module 114 may include one or more instruction sets that define a movement profile configured to cause bedside system 12 to move the distal tip of guide catheter 64 to the desired position. In one embodiment, procedure control module 98 may be configured to display several icons (such as icons 162, 164, or 166) on touch screen 18 each indicating a different bend angle or bend shape (e.g., a button for a 30 degree bend, a button for a 40 degree bend, a button for the Judkins Left 4 bend, a button for the Judkins Right 4 bend, etc.), and when the user pushes the button for a particular degree bend or bend shape, the instruction set of movement instruction module 114 associated with the selected icon is executed causing the distal tip of guide catheter 64 to move to the bend angle or bend shape associated with the selected icon.

In another embodiment, movement instruction module 114 may include sets of instructions specific to various types of catheter based procedures that may be performed using bedside system 12. For example, movement instruction module 114 may include one set of instructions that will be executed if bedside system 12 is being used to perform a diagnostic catheterization procedure, shown as diagnostic procedure instruction set 186, and another set of instructions that will be executed if bedside system 12 is being used to perform a therapeutic catheter procedure, shown as therapeutic procedure instruction set 188. In this embodiment, controls 16 may include at least one user input device (e.g., touch screen icons 162, 164, 166) that allows the user to select whether catheter procedure system 10 is going to be used for a diagnostic or therapeutic procedure. In this embodiment, a user input device (e.g., touch screen icon 162, 164, 166) of controls 16 may be associated with a diagnostic procedure and another user input device may be associated with a therapeutic procedure, and selection or operation of the associated user input device by the user activates diagnostic procedure instruction set 186 or therapeutic procedure instruction set 188.

In addition, diagnostic procedure instruction set 186 or therapeutic procedure instruction set 188 may include various subsets of instructions for various types of diagnostic or therapeutic procedures that may be performed using bedside system 12. In one such embodiment, a user input device (e.g., touch screen icon 162, 164, 166) of controls 16 may be associated with a specific type of therapeutic procedure, and selection or operation of the associated user input device activates the appropriate instruction set of therapeutic procedure instruction set 188 that is related to the specific type of therapeutic procedure to be preformed. For example, therapeutic procedure instruction set 188 may include a first instruction set associated with a stent placement procedure, a second instruction set associated with an angioplasty procedure, a third instruction set associated with an ablation procedure, etc. Thus, in this embodiment, the user will select the type of therapeutic procedure that is to be preformed via the associated user input device, and the instruction subset of therapeutic procedure instruction set 188 for the selected type of therapeutic procedure will be activated.

In other embodiments, movement instruction module 114 may include sets of instructions specific to various types of percutaneous devices that may be used with bedside system 12, shown as device specific instruction sets 190. For example, device specific instruction sets 190 may include a set of instructions for each different type, make and/or model of percutaneous devices that may be used with bedside system 12. In such an embodiment, the instruction set for a particular type, make or model of percutaneous device may account for the properties of the device (e.g., weight, diameter, surface friction, rigidity, etc.) to ensure that the percutaneous device is moved as expected by bedside system 12. In addition, the instruction set for a particular percutaneous device may based on the type of device being controlled by bedside system 12 (e.g., a guide wire, guide catheter, a working catheter, an angioplasty balloon, a stent, ablation catheter, imaging catheter, etc.).

Some percutaneous devices are designed to be moved or controlled in a particular way during treatment of a condition. Device specific instruction sets 190 may include one or more instruction sets to cause bedside system 12 to move such a percutaneous devices in a manner consistent with its design. For example, in one embodiment, device specific instruction sets 190 may include one or more instruction sets to allow bedside system 12 to control a device specially designed to traverse a chronic total occlusion (e.g., the CrossBoss CTO Catheter manufactured by BridgePoint Medical). In this embodiment, movement instruction module 114 includes an instruction set that allows bedside system 12 to rotate the CrossBoss CTO Catheter at its specified speed.

In another exemplary embodiment, device specific instruction sets 190 may include one or more instruction sets to allow bedside system 12 to control the Symplicity Catheter manufactured by Ardian, Inc. for the treatment of hypertension. The Symplicity Catheter emits low-power radiofrequency energy to deactivate certain renal nerves from within the renal artery to treat hypertension. In this embodiment, movement instruction module 114 includes an instruction set to cause the Symplicity Catheter to retract a certain distance, to rotate a certain amount, and to emit a pulse of radiofrequency energy following rotation and retraction. In this embodiment the retract distance and the rotation amount are determined to position the Symplicity Catheter in the proper locations to deactivate the proper number of renal nerves to treat hypertension.

Controller 40 also includes simulation module or subsystem 100, assist module or subsystem 102, mode selection module or subsystem 104, inventory module or subsystem 106, GUI module or subsystem 108, data storage module or subsystem 110, and record module or subsystem 112. Generally, simulation module 100 is configured to run a simulated catheterization procedure based upon stored vascular image data and also based upon a user's manipulation of controls 16. Generally, assist module 102 is configured to provide information to the user located at workstation 14 during a real and/or simulated catheterization procedure to assist the user with the performance of the procedure. Specific embodiments of controller 40, including specific embodiments of simulation module 100, and assist module 102, are described in detail in P.C.T. International Application No. PCT/US2009/055318, filed Aug. 28, 2009, which is incorporated herein by reference in its entirety. Other specific embodiments of controller 40, including specific embodiments of GUI module 108, are described in P.C.T. International Application No. PCT/US2009/055320, filed Aug. 28, 2009, which is incorporated herein by reference in its entirety.

Movement instruction module 114 has been described as including various instructions sets in various exemplary embodiments as discussed above. However, it should be understood that movement instruction module 114 may include any combination of one or more of the instruction sets discussed above. In any embodiment in which movement instruction module 114 includes more than one instruction set, controller 40 may be configured to select one or more proper instruction set to be activated for a particular procedure either automatically or based on a received user input.

In various embodiments, controller 40 may be configured to allow the user of controls 16 to choose which instruction set or sets of movement instruction module 114 to activate for a particular procedure. In one such embodiment, one or more user input device (e.g., touch screen icon 162, 164, 166, a button, switch, etc.) of controls 16 may be associated with a particular movement instruction set, and selection or operation of the associated user input device activates the instruction set of movement instruction module 114 related to the desired movement parameter or movement profile. Then, with one of the instruction sets activated via operation of the associated user input device, the percutaneous device is moved in accordance with the activated movement instruction set as the user manipulates controls 16 (e.g., a joystick).

In one embodiment, procedure control module 98 may display information associated with one or more of the available instruction sets of movement instruction module 114 from which the user may chose. For example, a list of available instruction sets (e.g., instruction set for pulsed axial movement, instruction set for corkscrew motion, instruction sets for different percutaneous devices, etc.) may be displayed on a display device. In this embodiment, the user may then select the desired instruction set from the list to activate that instruction set using a device such as a mouse or touch screen. When an instruction set of movement instruction module 114 is activated, control signal 116 and the resulting movement of percutaneous device is based upon the user's manipulation of controls 16 and based upon the activated instruction set. In one embodiment, controller 40 is configured to display a separate touch screen icon associated with each movement instruction set of movement instruction module 114. In another embodiment, each available instruction set may be displayed as a list (e.g., a drop-down menu) allowing the user to select the desired instruction set via an input device such as a mouse.

In other embodiments, controller 40 may be configured such that one or more movement instruction set of movement instruction module 114 may be active at one time. In this embodiment, the user may activate any combination of one or more instruction sets of movement instruction module 114 via the associated user input devices. In one embodiment, the user may select more than one instruction set from the list of available instruction sets. For example, the user may activate both the axial step movement profile and the rotational movement profile at the same time, such that operation of controls 16 causes bedside system 12 to move the percutaneous device both for rotation and pulsed axial advancement. As another example, the user may select one instruction set of the device specific instruction sets 190 for the device that the user is controlling via bedside system 12 and may select another instruction set for the type of movement (e.g., pulsed movement, corkscrew movement, etc.). In another embodiment, the user may also select an additional instruction set associated with the type of procedure being performed (e.g., diagnostic, therapeutic, etc.). In other embodiments, a subset of the available movement instruction sets of movement instruction module 114 may be selectable by the user (e.g., profiles 182 and 184), and another subset of the available movement instruction sets of movement instruction module 114 may be automatically selected by controller 40, as described in more detail below. Once one or more instruction sets of movement instruction module 114 are activated, bedside system 12 will be operated based upon the user's manipulation of controls 16 and based upon the one or more activated instruction set.

In some embodiments, procedure control module 98 may be configured to automatically select or activate one or more of the available instruction sets of movement instruction module 114 based upon data available to or received by controller 40. In one embodiment, the instruction set that is automatically activated is associated with a feature of the percutaneous device being controlled. In various embodiments, the feature of the percutaneous device may include the type, make, model and a physical property of the percutaneous device. In one such embodiment, the user may indicate the type of percutaneous device being used for a procedure, and procedure control module 98 may automatically activate the instruction set associated with that particular type of percutaneous device. The user may indicate the type of percutaneous device by any suitable means, for example, entry of the name, model number, or other identifying information of the percutaneous device via a keyboard, selection of the particular percutaneous device from a list, scanning of a barcode associated with the percutaneous device with a barcode reader in communication with controller 40, etc. In another embodiment, catheter procedure system 10 may include an RFID reader that reads an RFID tag containing identifying information associated with a percutaneous device that has been loaded into bedside system 12. The identifying information or data read by the RFID reader may then be communicated to procedure control module 98, and procedure control module 98 may select the appropriate instruction set from movement instruction module 114 based on the identifying information read by the RFID reader.

In one embodiment, assist module 102 may be configured to provide information to the user (e.g., via display on monitor 26 and/or 28, etc.) to aid in the selection of the proper instruction set of movement instruction module 114 for a particular procedure. In one embodiment, assist module 102 may display a suggestion to the user regarding which instruction set should be activated for a particular procedure. In one embodiment, the suggestion generated by assist module 102 may be based on analysis of image data of a patient acquired during a diagnostic or therapeutic procedure. In one embodiment, assist module 102 may be configured to assess one or more property (e.g., density, degree of calcification, etc.) of a lesion (e.g., an atherosclerosis, etc.), and may suggest a movement instruction set suitable for traversing the lesion with the percutaneous device. For example, if a particular lesion is identified to have a high degree of calcification, assist module 102 may select a movement instruction set suitable to allow the percutaneous device to traverse the lesion, such as a pulsed movement instruction set with a relatively low pulse duration may.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be used alone or in combination with any of the features, elements, or components of any of the other embodiments discussed above. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A workstation configured for operating a robotic catheter system comprising:

a user interface configured to receive a first user input;

a control system operatively coupled to the user interface, the control system configured to remotely control movement of at least a first percutaneous device and a second percutaneous device, wherein at least the first percutaneous device is moveable both for advancement and retraction along a longitudinal axis of the first percutaneous device and for rotation about the longitudinal axis of the first percutaneous device; and a device movement algorithm subsystem including at least one set of instructions stored in a memory, the at least one set of instructions defining at least one predetermined percutaneous device movement profile comprising a step distance, a step duration and a rest duration that define a series of advance pulsed axial steps for advancing the first percutaneous device along the longitudinal axis in a first direction;

wherein the at least one set of instructions define a series of retract axial steps for retraction of the first percutaneous device along the longitudinal axis in a direction opposite the first direction of the first percutaneous device resulting from the advance pulsed axial steps, the retract axial steps being interspaced with the axial advance steps resulting in a net advancement of the percutaneous device along the longitudinal axis in the first direction;

wherein the control system controls the first percutaneous device based upon both the first user input and the at least one predetermined percutaneous device movement profile of the device movement algorithm subsystem such that the movement of the first percutaneous device in accordance with the movement profile results in a series of pulsed axial steps.

2. The workstation of claim 1, wherein the at least one percutaneous device movement profile further comprises a rotation rate, such that movement of the first percutaneous device in accordance with the movement profile results in rotation of the first percutaneous device during advancement of the first percutaneous device, wherein the instructions provide the first percutaneous device to both rotate about and move axially along the longitudinal axis providing a corkscrew action of the first percutaneous device.

3. The workstation of claim 1, wherein the user interface is configured to receive a second user input defining a movement parameter of the movement profile.

4. The workstation of claim 3, wherein the movement parameter is at least one of a step distance, a step duration, a rest duration, and a rotation rate.

5. The workstation of claim 1, wherein the at least one set of instructions includes a first set of instructions and a second set of instructions;
wherein the user interface is configured to receive a second user input;
wherein the control system activates one or more of the first set of instructions and the second set of instructions based on the second user input; and
further wherein the control system controls the first percutaneous device based upon both the first user input and one or more activated sets of instructions of the device movement algorithm subsystem.

6. The workstation of claim 5, wherein the user interface further comprises:
a first control configured to receive the first user input;
a second control associated with the first set of instructions, the second control configured to receive the second user input; and
a third control associated with the second set of instructions, the second control configured to receive a third user input;
wherein the control system is configured to activate the first set of instructions in response to the second user input and to activate the second set of instructions in response to the third user input.

7. The workstation of claim 6, wherein the first control comprises a joystick, the second control comprises a first touch screen icon, and the third control comprises a second touch screen icon.

8. The workstation of claim 6, wherein both the first set of instructions and the second set of instructions are activated at the same time and the control system is configured to control the first percutaneous device based upon the first user input, the activated first set of instructions and the activated second set of instructions.

9. The workstation of claim 5, wherein the first set of instructions is activated in response to the second user input, wherein the control system is configured to automatically activate the second set of instructions based upon data received by the control system.

10. The workstation of claim 9, wherein the second set of instructions is associated with a feature of the first percutaneous device and the received data is indicative of the feature of the first percutaneous device.

11. The workstation of claim 10, wherein the feature of the first percutaneous device is at least one of the type, make, model, and a physical characteristic of the first percutaneous device.

12. The workstation of claim 10, wherein the data is received from an RFID tag associated with the first percutaneous device.

13. The workstation of claim 1, wherein the at least one set of instructions is based upon a type of the first percutaneous device.

14. The workstation of claim 1, wherein the at least one set of instructions is based upon a type of disease to be treated.

15. The workstation of claim 1, wherein the at least one set of instructions is based upon a type of procedure to be performed.

16. A catheter procedure system comprising:
a bedside system comprising:
a first percutaneous device actuating mechanism including an axial movement actuator configured to move a first percutaneous device along a longitudinal axis of the first percutaneous device and a rotation actuator configured to rotate the first percutaneous device about the longitudinal axis of the first percutaneous device; and
a second percutaneous device actuating mechanism; and
a remote workstation, the remote workstation comprising:
a user interface configured to receive a first user input;
a control system operatively coupled to the user interface and to the bedside system, the control system configured to remotely and independently control movement of the first percutaneous device and a second percutaneous device; and
a device movement algorithm subsystem including at least one set of instructions stored in a memory, the at least one set of instructions defining at least one predetermined percutaneous device movement profile comprising a step distance, a step duration and a rest duration that define a series of pulsed axial steps for advancing the first percutaneous device along the longitudinal axis in a first direction;
wherein the at least one set of instructions define a series of retract axial steps for retraction of the first percutaneous device along the longitudinal axis in direction opposite the first direction of the first percutaneous device resulting from the advance pulsed axial steps, the retract axial steps being interspaced with the axial advance steps resulting in a net advancement of the percutaneous device along the longitudinal axis in the first direction;
wherein the control system controls the first percutaneous device based upon both the first user input and the at least one predetermined percutaneous device movement profile of the device movement algorithm subsystem such that the movement of the first percutaneous device in accordance with the movement profile results in a series of pulsed axial steps.

17. The catheter procedure system of claim 16, wherein the at least one percutaneous device movement profile further comprises a rotation rate, such that movement of the first percutaneous device in accordance with the movement profile results in rotation of the first percutaneous device during advancement of the first percutaneous device; wherein the movement profile provides the first percutaneous device to both rotate about and move axially along the longitudinal axis providing a corkscrew action of the first percutaneous device.

18. The catheter procedure system of claim 16, wherein the user interface is configured to receive a second user input defining a movement parameter of the movement profile.

19. The catheter procedure system of claim 18, wherein the movement parameter is at least one of a step distance, a step duration, a rest duration, and a rotation rate.

20. The catheter procedure system of claim 16, wherein the at least one set of instructions includes a first set of instructions and a second set of instructions, wherein the user interface is configured to receive a second user input, wherein the control system activates one or more of the first set of instructions and the second set of instructions based on the second user input, and further wherein the control system controls the first percutaneous device based upon both the first user input and one or more activated sets of instructions of the device movement algorithm subsystem.

21. The catheter procedure system of claim 20, wherein the user interface further comprises:
   a first control configured to receive the first user input;
   a second control associated with the first set of instructions, the second control configured to receive the second user input; and
   a third control associated with the second set of instructions, the second control configured to receive a third user input;
   wherein the control system is configured to activate the first set of instructions in response to the second user input and to activate the second set of instructions in response to the third user input.

22. The catheter procedure system of claim 21, wherein the first control comprises a joystick, the second control comprises a first touch screen icon, and the third control comprises a second touch screen icon.

23. The catheter procedure system of claim 21, wherein both the first set of instructions and the second set of instructions are activated at the same time, and the control system is configured to control the first percutaneous device based upon the first user input, the activated first set of instructions and the activated second set of instructions.

24. The catheter procedure system of claim 20, wherein the first set of instructions is activated in response to the second user input, wherein the control system is configured to automatically activate the second set of instructions based upon data received by the control system.

25. The catheter procedure system of claim 24, wherein the second set of instructions is associated with a feature of the first percutaneous device and the received data is indicative of the feature of the first percutaneous device.

26. The catheter procedure system of claim 25, wherein the feature of the first percutaneous device is at least one of the type, make, model, and a physical characteristic of the first percutaneous device.

27. The catheter procedure system of claim 26, wherein the data is received from an RFID tag associated with the first percutaneous device.

28. The catheter procedure system of claim 16, wherein the at least one set of instructions is based upon a type of the first percutaneous device.

29. The catheter procedure system of claim 16, wherein the at least one set of instructions is based upon a type of disease to be treated.

30. The catheter procedure system of claim 16, wherein the at least one set of instructions is based upon a type of procedure to be performed.

* * * * *